(12) United States Patent
Risi et al.

(10) Patent No.: US 12,161,859 B2
(45) Date of Patent: *Dec. 10, 2024

(54) VESTIBULAR STIMULATION DEVICE

(71) Applicants: Cochlear Limited, Macquarie University (AU); University of Washington Center for Commercialization, Seattle, WA (US)

(72) Inventors: Frank Risi, Newtown (AU); Colin Irwin, Nice (FR); Jay T. Rubinstein, Seattle, WA (US); Felipe Santos, Boston, MA (US); James O. Phillips, Seattle, WA (US)

(73) Assignees: Cochlear Limited, Macquarie University (AU); University of Washington Center for Commercialization, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/162,340

(22) Filed: Jan. 31, 2023

(65) Prior Publication Data

US 2023/0173256 A1 Jun. 8, 2023

Related U.S. Application Data

(63) Continuation of application No. 17/145,583, filed on Jan. 11, 2021, now Pat. No. 11,596,786, which is a
(Continued)

(30) Foreign Application Priority Data

May 29, 2009 (AU) .............................. 2009902449

(51) Int. Cl.
*A61N 1/05* (2006.01)
*A61N 1/36* (2006.01)

(52) U.S. Cl.
CPC ......... *A61N 1/0526* (2013.01); *A61N 1/0551* (2013.01); *A61N 1/361* (2013.01)

(58) Field of Classification Search
CPC ..... A61N 1/0526; A61N 1/0551; A61N 1/361
See application file for complete search history.

(56) References Cited

U.S. PATENT DOCUMENTS

| 5,545,219 A | 8/1996 | Kuzma |
| 6,078,841 A | 6/2000 | Kuzma |
| (Continued) | | |

FOREIGN PATENT DOCUMENTS

WO 2010138915 A1 12/2010

OTHER PUBLICATIONS

International Application No. PCT/AU2010/000655, International Search Report mailed on Aug. 5, 2010, 6 pages.
(Continued)

*Primary Examiner* — Mallika D Fairchild
(74) *Attorney, Agent, or Firm* — Edell, Shapiro & Finnan, LLC

(57) ABSTRACT

A vestibular stimulation array is disclosed having one or more separate electrode arrays each operatively adapted for implantation in a semicircular canal of the vestibular system, wherein each separate electrode array is dimensioned and constructed so that residual vestibular function is preserved. In particular, the electrode arrays are dimensioned such that the membranous labyrinth is not substantially compressed. Furthermore, the electrode array has a stop portion to limit insertion of the electrode array into the semi-circular canal and is still enough to avoid damage to the anatomical structures.

8 Claims, 6 Drawing Sheets

Related U.S. Application Data continuation of application No. 16/237,794, filed on Jan. 2, 2019, now Pat. No. 10,888,696, which is a continuation of application No. 14/744,951, filed on Jun. 19, 2015, now abandoned, which is a continuation of application No. 13/375,141, filed as application No. PCT/AU2010/000655 on May 28, 2010, now Pat. No. 9,089,692.

(56)  References Cited

U.S. PATENT DOCUMENTS

| | | | |
|---|---|---|---|
| 6,314,324 | B1 | 11/2001 | Lattner et al. |
| 7,225,028 | B2 * | 5/2007 | Della Santina ........ A61N 1/372 |
| | | | 607/57 |
| 8,532,788 | B2 | 9/2013 | Zhulati et al. |
| 9,089,692 | B2 | 7/2015 | Risi et al. |
| 2002/0072781 | A1 | 6/2002 | Attner et al. |
| 2004/0215236 | A1 * | 10/2004 | Lattner .............. A61N 1/36036 |
| | | | 607/2 |
| 2007/0208403 | A1 | 9/2007 | Della Santina et al. |
| 2008/0312717 | A1 | 12/2008 | Gantz |
| 2010/0198103 | A1 | 8/2010 | Meadows et al. |
| 2011/0295352 | A1 | 12/2011 | Thenuwara et al. |

OTHER PUBLICATIONS

International Application No. PCT/AU2010/000655, Written Opinion mailed on Aug. 5, 2010, 6 pages.

Della Santina et al., A Multichannel Semicircular Canal Neural Prosthesis Using Electrical Stimulation to Restore 3-D Vestibular Sensation, IEEE Trans. Biomed. Eng., vol. 54, No. 6, Jun. 2007, pp. 1016-1030.

Gong et al., System Design and Performance of a Unilateral Horizontal Semicircular Canal Prosthesis, IEEE Trans Biomed. Eng., vol. 49, No. 2, Feb. 2002, pp. 175-181.

International Application No. PCT/AU2010/000655, Supplemental EP Search Report mailed on Feb. 12, 2014, 11 pages.

* cited by examiner

VESTIBULAR STIMULATION DEVICE

CROSS REFERENCE TO RELATED APPLICATIONS

This application is a continuation of U.S. application Ser. No. 17/145,583, filed on Jan. 11, 2021, which is a continuation of U.S. application Ser. No. 16/237,794, filed on Jan. 2, 2019, which is a continuation of U.S. application Ser. No. 14/744,951, filed on Jun. 19, 2015, which is a continuation of U.S. application Ser. No. 13/375,141, filed Feb. 7, 2012, entitled "Vestibular Stimulation Device," now U.S. Pat. No. 9,089,692, issued Jul. 28, 2015, which is a national stage application of PCT/AU2010/000655, filed on May 28, 2010, which claims priority to Australian Patent Application No. 2009902449, filed on May 29, 2009, the disclosures of which are hereby incorporated by reference herein in their entireties. To the extent appropriate, a claim of priority is made to each of the above disclosed applications.

GOVERNMENT LICENSE RIGHTS

This invention was made with government support under HHS-N-260-2006-00005-C awarded by National Institutes of Health (NIH). The government has certain rights in this invention.

TECHNICAL FIELD

The present invention relates to devices for stimulation of the vestibular system.

BACKGROUND TO THE INVENTION

The vestibular system is a portion of the inner ear which enables the sensation of angular and linear motion. Neural signals corresponding to this sensed motion are used by the brain to assist in a variety of processes including balance and determining orientation, and in related motor activities such as walking, standing, and visual orientation. The vestibular system includes the three semicircular canals and the otolithic organs. Various abnormalities of the vestibular system are known, and in severe cases they can result in significant disability for those so afflicted. In older persons, the loss of stability attendant upon vestibular dysfunction can lead to a greatly increased likelihood of a fall, and consequent loss of independence and mobility.

Meniere's disease is an abnormality of the vestibular system which affects approximately 1 in 2000 people worldwide. Meniere's has typical symptoms including periodic episodes of rotary vertigo or dizziness; fluctuating, progressive, unilateral or bilateral hearing loss; unilateral or bilateral tinnitus; and a sensation of fullness or pressure in one or both ears. It commonly begins with one symptom, and progresses to others. The symptoms of Meniere's are highly variable between patients, and it is relatively difficult to diagnose with certainty.

Approximately 85% of affected people can be treated with measures such as medication, dietary changes, lifestyle changes, or behavioral therapy. However, the remaining 15% are not assisted sufficiently by these measures, and typically turn to one of a variety of surgical procedures, all of which have significant downsides.

It has been proposed to provide a vestibular stimulator using electrical stimulation in order to treat vestibular disease. U.S. Pat. No. 6,314,324 discloses a vestibular stimulation device, using either electrodes placed externally, or implanted neural stimulation electrodes. U.S. Pat. No. 7,225,028 to Santina et al discloses a dual cochlear and vestibular stimulator.

It is an object of the present invention to provide an electrode array suitable for implantation within one or more semicircular canals of a user, so as to facilitate vestibular stimulation.

SUMMARY OF THE INVENTION

In a broad form, the present invention proposes a vestibular electrode array structure, with the electrode arrays being constructed so that each array will fit within one of the semicircular canals while substantially preserving the existing rotational sensitivity of the semicircular canal.

According to one aspect, the present invention provides a vestibular stimulation array, including one or more separate electrode arrays each operatively adapted for implantation in a semicircular canal, wherein each separate array is dimensioned and constructed so that the residual vestibular function is preserved.

In a preferred form, the array is dimensioned and constructed so that it may be inserted within one of the canals without substantially compressing the membranous labyrinth.

The present invention also encompasses a vestibular stimulation device incorporating such an array.

According to another aspect, the present invention provides a method of vestibular stimulation, wherein a vestibular stimulation array is implanted into one or more of a user's semicircular canals, said array being dimensioned and constructed so as to be inserted into a semicircular canal whilst still preserving residual vestibular function and, preferably, without substantially compressing the membranous labyrinth, said array being adapted to deliver electrical stimuli.

According to another aspect, the present invention provides a method of operatively positioning a vestibular stimulation electrode array, the array being connected to a stimulation device adapted to measure neural responses to electrical stimuli, wherein the electrode array is positioned in an estimated position, the stimulation device is operated so as to produce stimuli from the array, and the neural response to said stimuli measured, the process being repeated if required at different positions, so that the array is positioned at the position where the most desirable neural response is obtained.

According to another aspect, the present invention provides a vestibular stimulation array, including a body, the body being formed as a base section branching into three separate canal arrays, each canal array including an insertable portion adapted for placement into a semicircular canal, each insertable portion including at least three stimulating electrodes, each of said electrodes being adapted to selectively deliver electrical stimulation, wherein the insertable portion has a diameter of less than about 150 µm.

BRIEF DESCRIPTION OF THE DRAWINGS

Illustrative embodiments of the present invention will now be described with reference to the accompanying figures, in which.

DETAILED DESCRIPTION

The present invention will be described with reference to a particular illustrative example, which is a device intended for use in a vestibular stimulation system. The present invention is applicable to a system with implanted components, powered and controlled from an external device, or to a fully implanted system, with a remote control or similar device. It may be incorporated with a cochlear implant or other hearing prosthesis, or be a standalone device. It will be appreciated that the present implementation is described for illustrative purposes, and its features are not intended to be limitative of the scope of the present invention. Many variations and additions are possible within the scope of the present invention.

Figure 1:
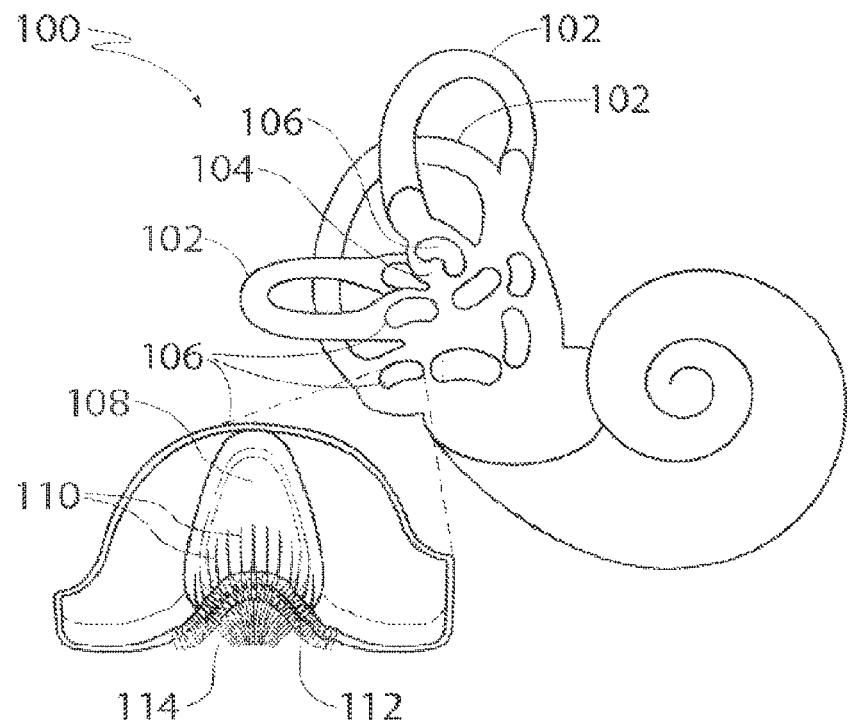
FIG. 1 is a general schematic illustration of the anatomical structures of the vestibular system.

FIG. 1 illustrates the structures of the inner ear, with particular reference to the vestibular system 100. The three semi-circular canals 102 are shown, each being arranged more or less orthogonal to each other. Each canal is filled with endolymph fluid, and upon rotation of the head with a component of motion in the appropriate direction, fluid is caused to move within the canal. At the base of each canal is the ampula 104 and the related crista 106. Within the crista 106 is the cupula 108 which contains hair bundles 110 connected to hair cells 112, and in turn to nerve fibres 114. When the fluid moves, the hair cells 112 are stimulated, and produce a corresponding neural signal.

Figure 2:
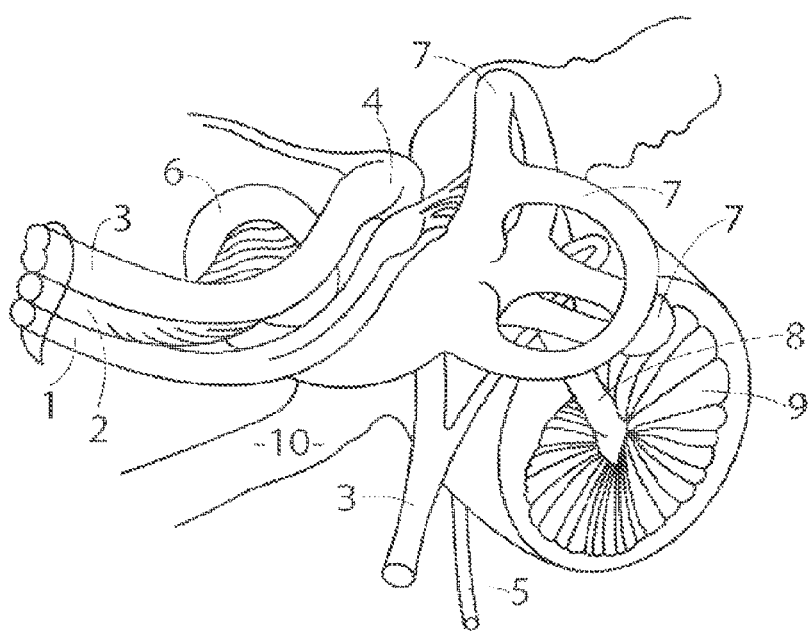
FIG. 2 is a more detailed illustration of the semicircular canals and related structures.

FIG. 2 illustrates in more detail the location and orientation of the vestibular labyrinth relative to cranial nerves VII and VIII and selected structures of the inner and middle ear. Illustrated are Nervus vestibularis 1, Nervus cochlearis 2, Nervus intermediofacialis 3, Ganglion geniculi 4, Chorda tympani 5, Cochlea 6, semicircular canals 7, Malleus 8, tympani 9, and ear canal 10.

The illustrative embodiment which will be described is intended to be used in a relatively simple, constant stimulation system. This is intended to be operable by a user when they determine that they have symptoms indicating the onset of an attack, or alternatively in a preventative mode, in which the device is operated to prevent the onset of an attack. However, it is envisaged that the system could be implemented in a manner which is connected to a monitor that automatically enables/disables stimulation dependent on early indicators of an attack. In another alternative, the system could be operated in constant "on" mode to maintain a manageable level of vestibular function in cases of severe vestibular dysfunction. Direct electrical stimulation of the vestibular system by implanting an electrode array atraumatically within one or more semicircular canals provides an alternative to other available medical or surgical interventions.

The proposed implementation consists of an external processor; transmit coil (transcutaneous link); implant; electrode arrays; and remote control or other activation device. For the purpose of treating Meniere's disease, one or more of the electrodes would be electrically stimulated to simulate the absent spontaneous neural activity. It will be appreciated that other implementations, for example a fully implanted system, are possible.

Figure 4:
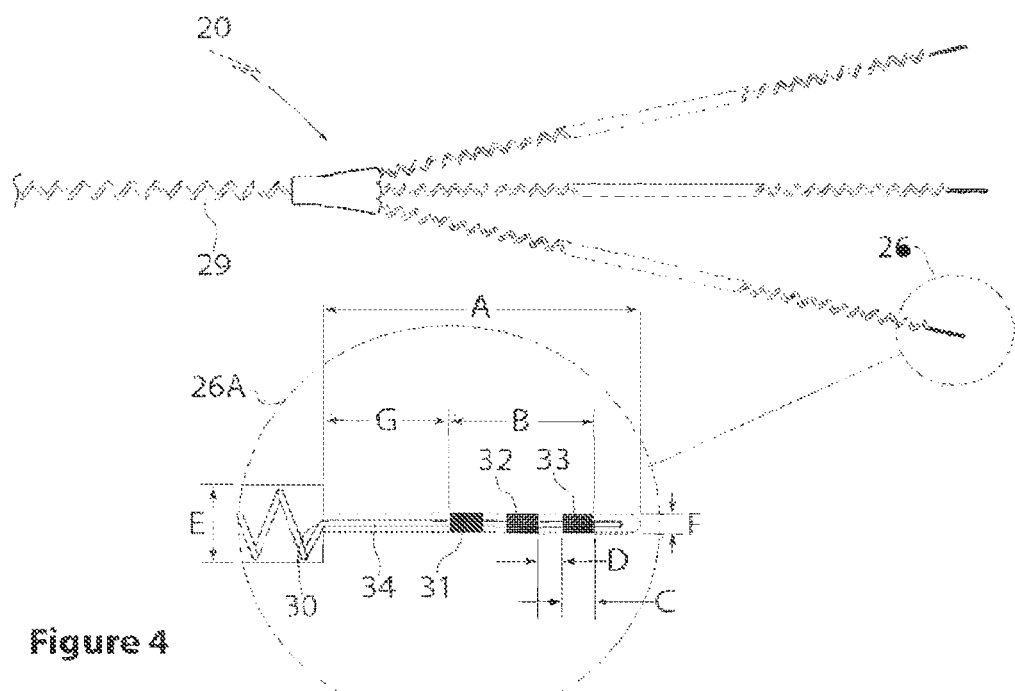
FIG. 4 is a more detailed view of the implementation of FIG. 3.
Figure 5:
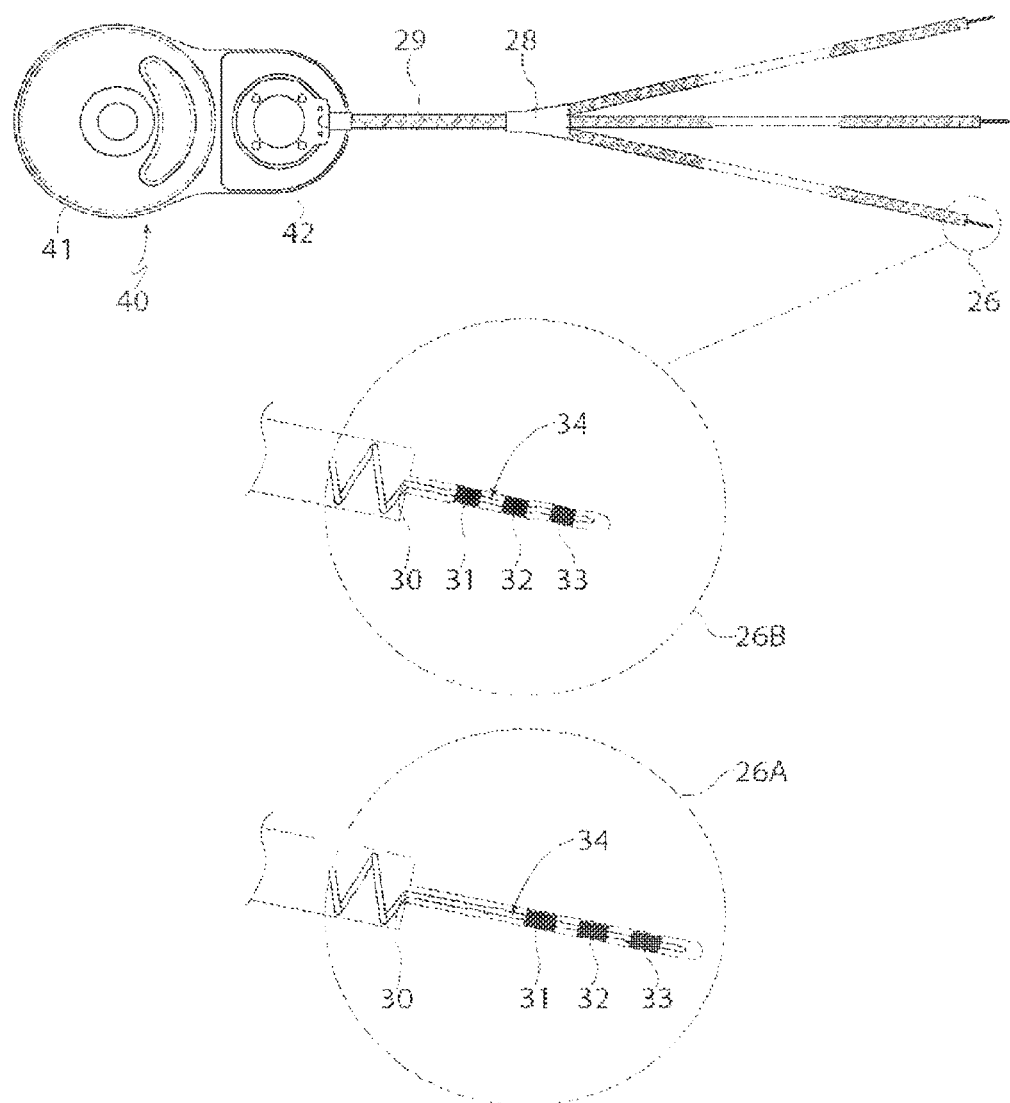
FIG. 5 is a detailed view of the implementation of FIG. 3, including two alternative electrode array structures.
Figure 6:
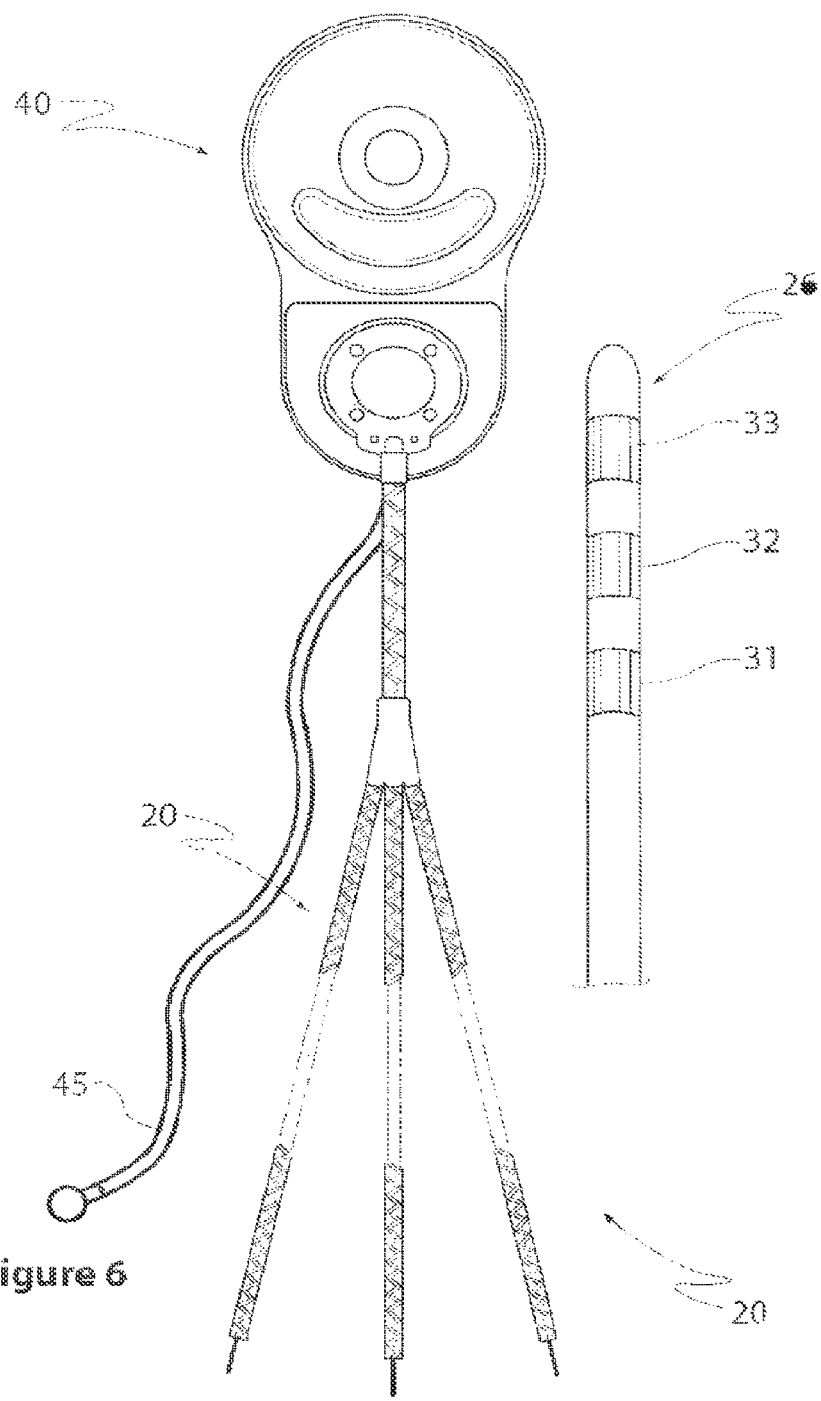
FIG. 6 is a photograph of a device according to FIG. 5.

One suitable implementation is shown in FIGS. 4, 5 and 6. The stimulation device 40, and associated external power supply/stimulation controller, is a conventional cochlear implant stimulator device and external speech processor (not shown), with a customized electrode array (the latter will be discussed further below). This stimulator device according to this implementation is the Freedom receiver/stimulator unit, available commercially from Cochlear Limited. The speech processor and associated stimulation system is capable of much more sophisticated stimulation than is required for the present application, at least in so far as a simple implementation is concerned.

For the purposes of understanding the cochlear implant stimulation system, in this case being used for vestibular stimulation, the following explanation is provided. However, the reader should review the commercially available cochlear stimulation devices if further detail is required.

Cochlear prostheses generally include an external, wearable control unit that determines a pattern of electrical stimulation that is provided to an implanted stimulator unit containing active circuitry in a hermetic enclosure. Electrical stimuli are delivered through electrodes to provide electrical stimulation of auditory nerve cells.

Once implanted, the electrodes of the electrode array receive stimulation signals from a stimulator unit. The stimulator unit is typically electrically connected to the electrode array by an electrical lead. The stimulator unit is positioned within a housing that is implantable within the patient, and is typically implanted within a recess in the bone behind the ear posterior to the mastoid. When implanted, the housing preferably contains, in addition to the stimulator unit, a receiver unit adapted to receive signals from a controller. The controller is, in this example, mounted external to the body behind the pinna of the patient such that signals are transmitted transcutaneously through the skin of the patient.

The signals travel from the controller to the receiver unit and vice versa. The receiver unit includes a receiver antenna, such as an antenna coil, adapted to receive radio frequency (RF) signals from a corresponding transmitter antenna, such as an antenna coil, worn externally of the body. The radio frequency signals may comprise frequency modulated (FM) signals, but could alternatively be modulated in any suitable way, using, amplitude, frequency or phase, using either analog or digital techniques. In general, the modulation should be chosen in order to maximize both the data and power efficiency of the link. It should be appreciated that the receiver antenna may also transmit signals, and that the transmitter antenna may receive such signals. The transmitter antenna coil is preferably held in position adjacent the implanted location of the receiver antenna coil by way of respective attractive magnets (not shown) mounted centrally in, or at some other position relative to, the coils.

The external controller in this example includes a processor (not shown) adapted to encode a suitable stimulation signal, for example in response to the device being turned on by the user. Such a signal would include data defining, for example, the mode of stimulation, current level, and which electrodes are to be stimulated. As the present invention contemplates the use of three separate electrode arrays, the stimulation may occur on more than one array simultaneously, or alternatively, sequentially. The encoded sequence is transferred to the implanted receiver/stimulator unit using the transmitter and receiver antennae. The implanted receiver/stimulator unit demodulates the signals and allocates the electrical pulses to the appropriate electrode. The external controller may further include a power supply (not shown). The power supply may comprise one or more rechargeable batteries. The transmitter and receiver antennae are used to provide power via transcutaneous induction to the implanted receiver/stimulator unit and the electrode array.

It is contemplated that the implanted arrays should be adapted to deliver both monopolar and bipolar stimulation. Bipolar stimulation occurs when a current flows from one electrode to another electrode of the same array, that is, in the same canal. Monopolar stimulation occurs when current flows between an electrode within the canal and an electrode external to the canal, for example a separate implanted electrode external to the canal. Depending on the stimulation current required to elicit a response bipolar may be advantageous in minimizing interaction with adjacent semicircular canals. At least two channels, typically one intracanal and one inter canal, are also required for Neural Response Telemetry which has been shown to be important during surgery for electrode placement.

When there is no movement, the normal vestibular system generates constant regular activity, i.e., the neurons in the semicircular canal fire at a constant rate. Without limitation to the present invention, Meniere's disease is believed to cause an increase in the pressure of the endolymph in the semicircular canals. This in turn causes the neurons to cease their regular firing.

The objective of stimulation is to simulate this constant firing through delivery of electrically evoked afferent activity. This may, according to the present implementation, be unmodulated. However it is contemplated that other implementations may be modulated, for example in frequency or amplitude, in order to provide more complex user percepts. Clinically a stimulation method would be chosen so that it delivers the required stimulation (and desired percept); provides no interference from one canal to another; and operates at the lowest level of power. The electrical stimuli required are generally of a much lower complexity and at lower rate pulse trains than for auditory stimulation. For example, the electrical stimuli may be provided as biphasic pulses at 100-200 Hz, 400 us phase width, 8 us phase gap and currents of between 20-100 uA. These figures are indicative only, and implementations may use other parameters.

A particular feature of implementations of the present invention is that an electrode array is intended to be inserted into each of the semi-circular canals whilst preserving any residual vestibular function. This is achieved using a suitable dimension, for example for a circular array, a diameter less than 150 microns. Other specific characteristics, relating to length, a stopper to limit penetration, and stiffness assist in this objective, as will be explained further below.

The principal issue with preserving existing function is to avoid damage to existing structures, and the present invention contemplates electrode designs intended to achieve this. Whilst the implementation described uses a diameter limitation approach and an electrode array similar in structure to a cochlear implant device, it will be appreciated that this result may be achieved by selection of materials, alternative shapes for the array body and electrodes, and other mechanisms, all of which are encompassed within the general inventive scope.

For example, the array may have a special coating or be formed from a special material to assist in insertion. Specific electrode designs, in either or both mechanical and structural feature, or in the electrical structure, may assist in achieving the objective. Similar structures, materials and approaches could be used as for cochlear electrode arrays, especially hybrid arrays intended to preserve existing auditory function. The array could, for example, be drug eluting in order to minimise reaction to foreign bodies, or to reduce the risk of post-implantation infection.

Figure 3:
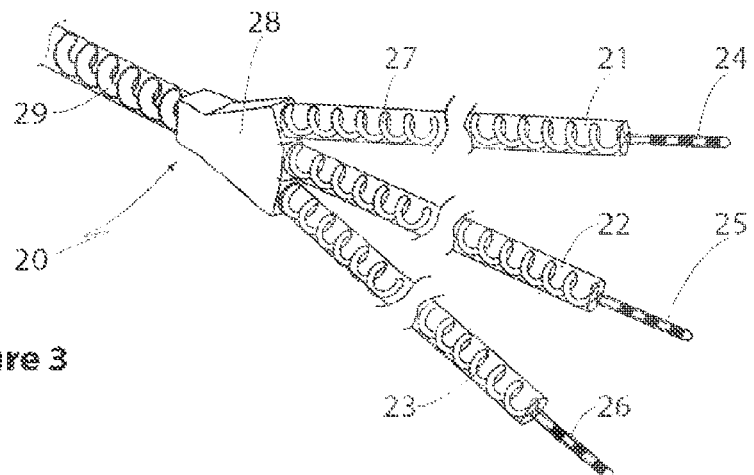
FIG. 3 is a schematic view of one implementation of an array according to the present invention.

According to the preferred implementation, a number of small electrode arrays for surgical placement between the bony labyrinth and the membranous labyrinth of each semicircular canal (superior, posterior and lateral) of the vestibular labyrinth. Referring to FIG. 3, the electrode array 20 consists of an electrode lead 29 which trifurcates at junction 28 into three leads 21, 22, 23, each intended for one of the semicircular canals. Each lead 21, 22, 23 terminates in a respective electrode array 24, 25, 26, intended for insertion into one of the semicircular canals. Each array (illustratively 26) has three electrodes 31, 32, 33 for applying stimulation. The array further includes a stiffening member to provide the necessary mechanical characteristics, as will be discussed further below.

The aim of the vestibular electrodes is to provide an electrical interface to the vestibular periphery without damaging or destroying residual vestibular function, in order to restore a level of vestibular function for people with disorders such as Meniere's disease.

The electrode array is designed for vestibular stimulation, and has a number of special features.

As can be seen from FIGS. 3, 4 and 5, the array 20 allows the surgical placement of three individual electrode arrays 24, 25, 26 to either one, two or all semicircular canals. The trifurcated lead allows for ease of surgical placement by providing a single lead 29 which branches into three leads 21, 22, 23 and electrode arrays 24, 25, 26 that can be individually implanted. The trifurcated structure improves lead reliability (impact, fatigue, stress, etc.), compared to having three separate leads exiting the stimulator, and simplifies the feedthrough structure from the stimulator. In the event that explantation is required, this structure reduces the time required and simplifies the surgical removal of one or all electrodes, or the entire device, compared to having three separate leads exiting the stimulator.

FIGS. 4 and 5 illustrate detailed views of the electrode array 26, designated 26A and 26B in FIGS. 4 and 5. The length A of each electrode array is preferably 2.5 mm. An alternative array is illustrated, with a length A, or insertion depth, of 1.7 mm. This is illustrated by the electrode array of 26B appearing shorter than that of 26A. In the preferred form, the electrode array span B is 1.15 mm, the individual electrode length C is 0.25 mm across and the electrode gap D is 0.2 mm. The lead before the insertion part has a larger diameter E, illustratively 0.64 mm, as compared to the insertion part F, which is 0.15 mm in diameter. This can also be seen in FIG. 7. The electrode array begins a distance G, which is preferably 1 mm, from the end of the larger diameter lead. An embedded stiffener 34 helps to keep the electrode array rigid.

The illustrated arrangement of electrode arrays allows for the placement of one electrode array in one semicircular canal, with the remaining electrode arrays placed safely within the mastoidectomy cavity for possible future implantation in the remaining semicircular canals. In this case, only the implanted array is used for stimulation. The remaining electrode arrays could also be used for possible otolithic stimulation via implantation of the vestibule, possibly via a round or oval window approach, or via the common crus.

FIG. 6 shows one implementation of the invention, using a conventional cochlear stimulation device 40. The device includes the trifurcated lead 20, as well as a reference electrode 45. The detail shows an enlarged view of the array, showing the electrodes 31, 32, 33.

Figure 8:
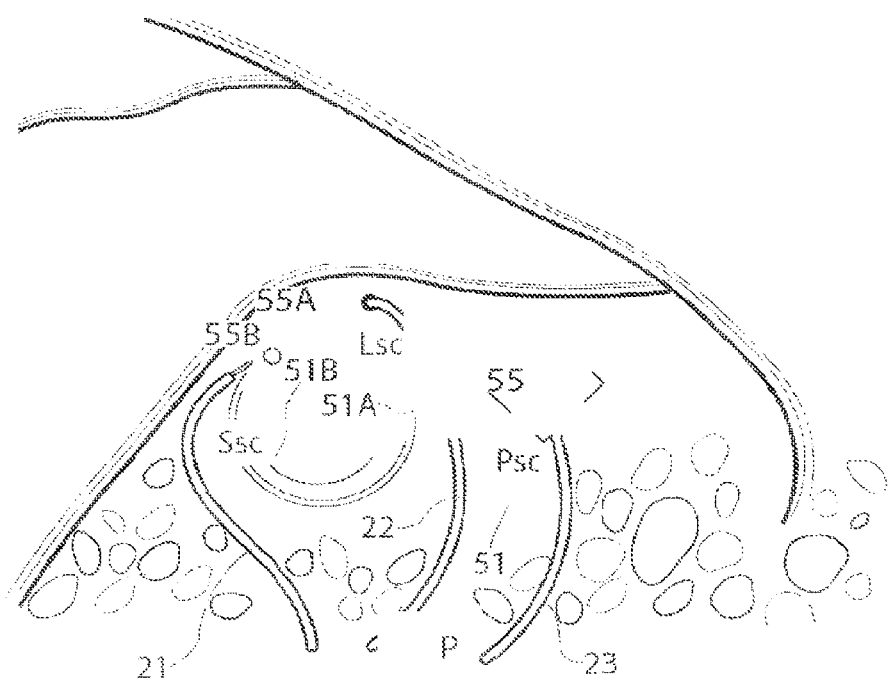
FIG. 8 is a schematic view of the implanted arrays.
Figure 9:
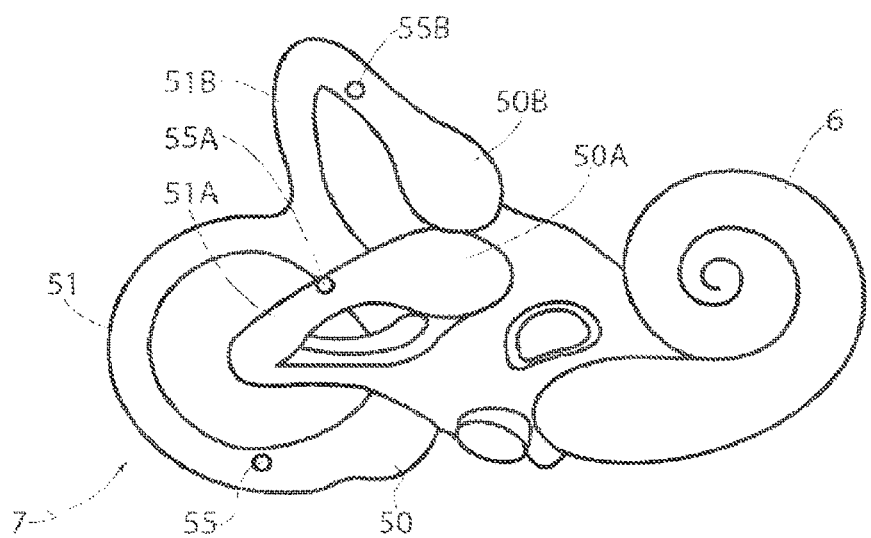
FIG. 9 is an illustration showing appropriate openings for inserting electrode arrays into the semicircular canals.

FIG. 9 illustrates suitable surgical openings 55, 55A, 55B in the posterior 51, superior 51B and lateral 51A semicircular canal, through which the electrode array 26 may be implanted. In each case, the respective ampulla 50, 50A, 50B can be seen. FIG. 8 shows the arrangement post-implantation, with the posterior semicircular canal (Psc) 51, the lateral semicircular canal (Lsc) 51A and the superior semicircular canal (Ssc) 51B shown only in their general positions behind a tissue wall, although the surgical openings 55, 55A and 55B and the leads 21, 22 and 23 are shown extending through their respective surgical openings.

Figure 7:
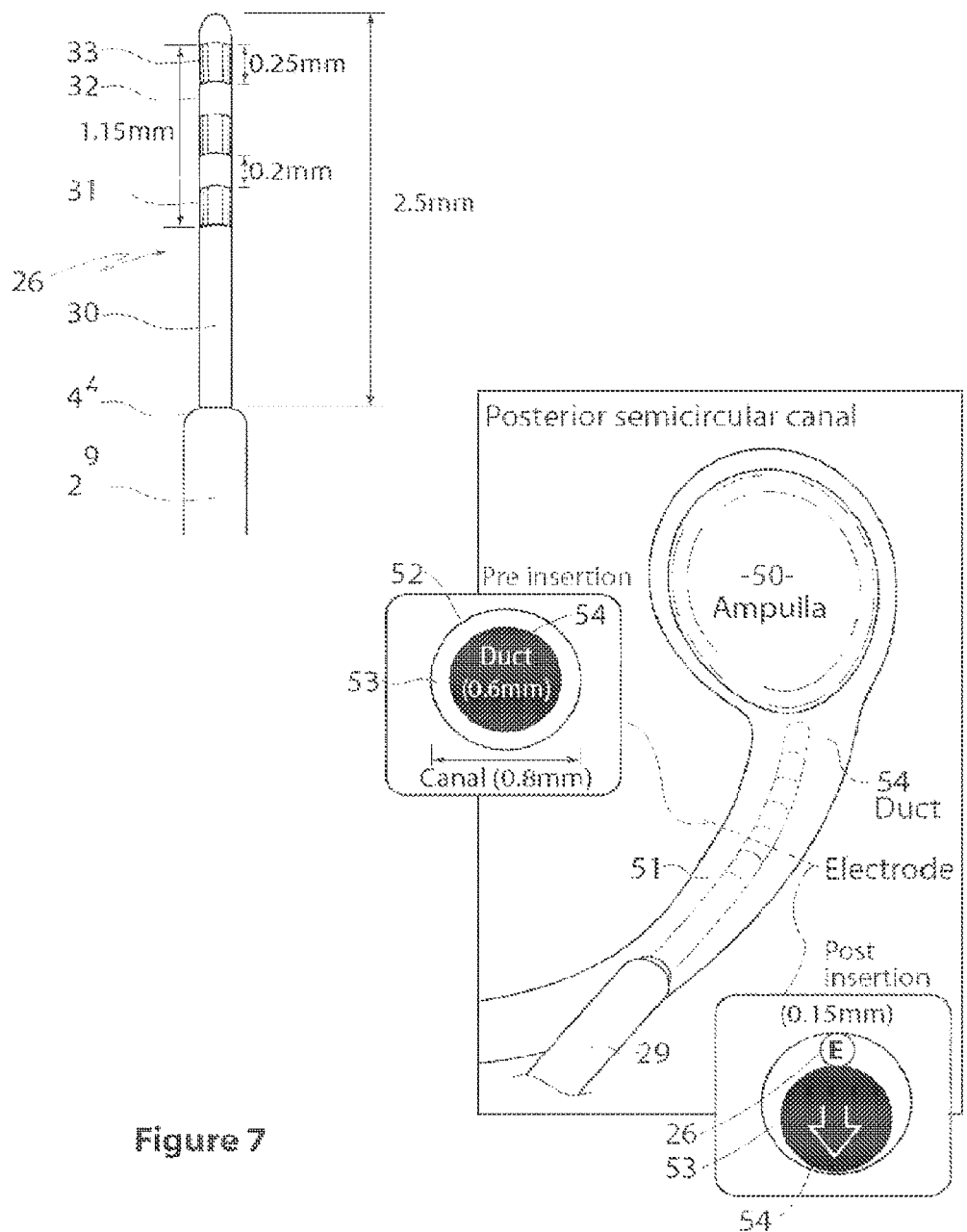
FIG. 7 is a view, partly in section, showing an array and a conceptual view of its preferred operative position and placement.

FIG. 7 shows one of the arrays being inserted into the opening, and its correct placement. The array 26 is inserted within the canal, proximate to the ampulla 50, between the bony labyrinth 52 and the membranous labyrinth 53. Studies have indicated that a better response to stimulation is achieved if the electrodes are proximate to the ampulla, however, it is generally considered important that the electrodes do not contact the ampulla. FIG. 7 also illustrates the appropriate fit of the electrode array-once in position, as can be seen in the post insertion drawing, the electrode array 26 lies next to, but not compressing or penetrating the membranous labyrinth 53, with duct 54 intact. The diameter of the array is selected to be sufficiently small to achieve this.

It is preferred that the insertion depth is controlled, so as to prevent the potential for damage to the ampulla. This has been identified from anatomical studies as 2-3 mm. In a preferred form, the part of the array for insertion is 2.5 mm long, and a stopper is provided to prevent further insertion. This may suitably take the form of an increased diameter of the lead distal to the electrode array itself. These features can be seen from FIGS. 6 and 7.

A small piece of fascia may be placed around the electrode array distal to the stopper, so that sealing of the 'canalostomy' can be promoted. It is important to minimize the exposure of perilymph. A platinum collar or mesh material could be incorporated to promote sealing.

The trifurcated lead is preferably between 15-45 mm, suitably 30 mm, in length. This has been identified via animal studies and cadaver studies as providing appropriate access and fixation. The placement of the trifurcated parts at suitable mutual angles, for example 20-40Q, facilitates surgical placement into each semicircular canal.

It is desirable that the array have sufficient stiffness and dynamics such that the electrode can be placed reliably within the labyrinth. The electrode array according to this implementation incorporates a stiffening member with unique characteristics, allowing the electrode array to be of the required diameter, yet of sufficient stiffness to insert to the desired depth between the bony labyrinth and the membranous labyrinth of each semicircular canal. The array should have a stiffness allowing a single stroke atraumatic insertion to the required depth in the canal. On the other hand, it must also have sufficient flexibility to deflect and avoid damage to the delicate anatomical structures. If the array is too stiff, it would be more prone to pierce or compress the delicate anatomical structures: if it is too soft or flexible, the electrode array may buckle and deform during insertion, and thereby cause trauma.

It has been determined by surgical trials, on animals and cadavers, that a suitable stiffness is comparable to 0.12 mm platinum wire. However, it will be appreciated that other values may be used in other implementations, noting the considerations mentioned above. It would also be possible to use a removable stiffening or insertion member, or to have variable flexibility.

The array must be operatively placed within the labyrinth whilst preserving vestibular function/sensitivity, but providing robust electrical stimulation of the vestibular periphery. It should allow for the use of soft surgery, including a small labyrinthotomy to gain access to and to preserve the membranous canal. The electrode array should insert between the bony labyrinth and the membranous labyrinth, without compressing the membranous labyrinth. It is preferred that the electrode array, or at least the part for insertion into the canal, has a diameter of 150 microns or less. This has been identified via cadaver and animal studies as optimal.

It is preferred that each array has a sufficient number of electrodes to permit both monopolar and bipolar stimulation, as well as to provide sufficient redundancy in the event of individual electrode failure. It is preferred that a suitable reference electrode is also provided as a return path for monopolar stimulation. A minimum of three electrodes in each array is preferred, as illustrated, however, a larger or smaller number of electrodes may be use to provide the same effect or to provide a subset of the above capabilities. It may be possible to have additional electrodes, however, appropriate criteria for electrode dimensions and charge density characteristics discussed elsewhere should be met. The electrodes also facilitate NRT measurements to optimize placement during implantation.

Initial implantation away from the ampulla of the lateral canal produced small responses at high current thresholds that were not in the canal plane. These were associated with limited dynamic range (current limits and recruitment of facial nerves were a problem).

Revision of the electrode placement closer to the ampulla produced thresholds an order of magnitude lower, and no cross talk to the facial nerve.

Precise electrode placement near the ampullae of the semicircular canals is critical for robust activation of the vestibular system, as determined by eye movements in response to electrical stimulation and the ocular reflex. The ocular reflex is a function of vestibular stimulation. Electrode placement that is too shallow, or too deep, results in weak or absent vestibular responses. Fortunately a reliable intraoperative tool for assisting in optimal electrode placement has been developed. Animal trials have demonstrated that, like the cochlear nerve, the vestibular afferents produce an electrically-evoked compound action potential (ECAP) that can be recorded from the implant using standard clinical Neural Response Telemetry software. When these responses can be recorded, robust electrically-evoked eye movements are obtained. When the responses cannot be recorded, no or minimal eye movements are obtained from stimulation.

Correctly positioned electrodes produce large, higher velocity nystagmic eye movements, slow phase velocities that scale with the frequency of stimulation, slow phase velocities that scale with the stimulus current, velocities greater than 50 degrees/s and amplitudes great than 10 degrees.

Whilst the present invention has been described with reference to a simple form of vestibular stimulation, it will be appreciated that the present invention could be used in conjunction with a more complex system. It could be applied, for example, with a vestibular prosthesis which operates to replicate impaired vestibular function using sensors for orientation and/or acceleration and corresponding electrical stimuli. Such systems may be of assistance in treating conditions such as bilateral vestibular hypofunction or are flexia and unilateral labyrinthitis.

What is claimed is:

1. A method comprising:
    inserting at least one electrode array of a vestibular device into a recipient, wherein the at least one electrode array comprises one or more electrodes electrically connected to a stimulator unit so as to form at least part of a vestibular stimulation device;
    after the at least one electrode array is inserted into the recipient, delivering one or more first electrical stimulation signals to a vestibular system of the recipient with the one or more electrodes;
    obtaining, via the one or more electrodes, one or more electrically evoked compound action potentials (ECAPs) generated by the vestibular system in response to the one or more first electrical stimulation signals;
    analyzing the one or more ECAPs generated by the vestibular system;
    setting, based on the analyzing, one or more parameters of the vestibular device;
    after the one or more parameters have been set, monitoring, with the vestibular device, one or more indicators of a balance disorder of the recipient;
    generating one or more second electrical stimulation signals based on the monitoring of the one or more indicators and the one or more parameters; and
    delivering the one or more second electrical stimulation signals to vestibular tissue of the recipient with the one or more electrodes.

2. The method of claim 1, wherein generating electrical stimulation based on the monitoring of the one or more indicators comprises:
    generating the electrical stimulation signals via the stimulator that is disposed in an implantable housing and electrically connected to the one or more electrodes via a lead.

3. The method of claim 1, wherein generating the one or more second electrical stimulation signals based on the monitoring of the one or more indicators comprises:
    generating the one or more second electrical stimulation signals without respect to a communication from a source external to the recipient.

4. The method of claim 1, further comprising:
    generating the one or more second electrical stimulation signals for delivery to a first portion of a vestibular system; and
    generating secondary electrical stimulation for delivery to a second portion of the vestibular system.

5. The method of claim 4, further comprising:
    generating the one or more second electrical stimulation signals for delivery to the first portion of the vestibular system with at least one of an amplitude, a frequency, a phase gap, or a pulse width that is selected to minimize interference with the secondary electrical stimulation delivered to the second portion of the vestibular system.

6. The method of claim 1, wherein the at least one electrode array has a stiffness such that the at least one electrode array can be inserted to a selected depth in an inner ear of the recipient.

7. The method of claim 1, wherein the one or more electrodes comprise a plurality of electrodes arranged in a linear array.

8. The method of claim 1, wherein delivering the one or more second electrical stimulation signals to vestibular tissue of the recipient via the one or more electrodes comprises:
    delivering otolithic stimulation to the recipient.

* * * * *